United States Patent [19]

Horie et al.

[11] Patent Number: 4,973,536

[45] Date of Patent: Nov. 27, 1990

[54] ELECTROPHOTOGRAPHIC PHOTORECEPTOR CONTAINING PHTHALOCYANINE AND HYDRAZONE

[75] Inventors: Seiji Horie; Naonori Makino; Hideo Sato, all of Kanagawa, Japan

[73] Assignee: Fuji Photo Film Co., Ltd., Kanagawa, Japan

[21] Appl. No.: 349,943

[22] Filed: May 8, 1989

Related U.S. Application Data

[63] Continuation of Ser. No. 86,451, Aug. 18, 1987, abandoned.

[30] Foreign Application Priority Data

Aug. 18, 1986 [JP] Japan .................................. 61-191773

[51] Int. Cl.⁵ .............................................. G03G 5/10
[52] U.S. Cl. .......................................... 430/59; 430/76
[58] Field of Search ........................ 430/96, 76, 58, 59

[56] References Cited

U.S. PATENT DOCUMENTS

| | | | |
|---|---|---|---|
| 4,423,130 | 12/1983 | Horie et al. | 430/76 |
| 4,471,039 | 9/1984 | Borsenberger | 430/76 |
| 4,592,984 | 6/1986 | Nishigaki | 430/59 |
| 4,675,262 | 6/1987 | Tanaka et al. | 430/58 |
| 4,814,245 | 3/1989 | Horie et al. | 430/59 |

*Primary Examiner*—John L. Goodrow
*Attorney, Agent, or Firm*—Sughrue, Mion, Zinn Macpeak & Seas

[57] ABSTRACT

An electrophotographic photoreceptor is described, comprising a photosensitive layer disposed on a conductive substrate, said photosensitive layer having a laminated structure comprising an electric charge generating layer and an electric charge transporting layer, said electric charge generating layer containing a phthalocyanine pigment which is selected from ε-type copper phthalocyanine, X-type or τ-type phtalocyanine, indium chloride phthalocyanine, calcium chloride phthalocyanine, and magnesium phthalocyanine, one of the benzene rings of the aluminum chloride or indium chloride phthalocyanine being optionally monochlorinated, and said electric charge transporting layer containing at least one hydrazone compound represented by formula (I) or (II) as set below:

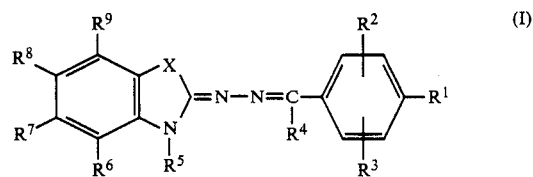

wherein the substituents are as defined in the specification.

7 Claims, No Drawings

ELECTROPHOTOGRAPHIC PHOTORECEPTOR CONTAINING PHTHALOCYANINE AND HYDRAZONE

This is a continuation of application Ser. No. 07/086,451, filed Aug. 18, 1987, abn.

FIELD OF THE INVENTION

The present invention relates to an electrophotographic photoreceptor having a photosensitive layer disposed on a conductive substrate, the photosensitive layer having a laminated structure comprising an electric charge generating layer and an electric charge transporting layer.

BACKGROUND OF THE INVENTION

Basic characteristics required for an electrophotographic photoreceptor include (1) the characteristic that it can be electrified to appropriate potential in a dark place, (2) the characteristic that the electric charge is substantially not dissipated and lost in a dark place, and (3) the characteristic that the electric charge can be rapidly dissipated and lost by irradiating it with light.

Inorganic substances such as selenium, cadmium sulfide, and zinc oxide that have been used to date have many merits, but, at the same time, various deficiencies. For example, selenium, now in wide use, sufficiently meets the above-mentioned conditions (1) to (3), but it has defects in that conditions for preparing it are difficult, it has a high production cost, it is not flexible, it is difficult to process into a belt shape, and it is very sensitive to thermal or mechanical shock so that it must be handled carefully. Cadmium sulfide or zinc oxide is dispersed in a resin as a binder and is used for an electrophotographic photoreceptor, but the phoptoreceptor has deficiencies in mechanical characteristics such as evenness, hardness, tensile strength, friction resistance, and the like, so that it is impossible to use it repeatedly as such.

In recent years, electrophotographic photoreceptors using various organic substances have been proposed to overcome the above-mentioned deficiencies of photoreceptors comprising inorganic substances, and some of them have been put into practice. Examples include an electrophotographic photoreceptor comprising poly-N-vinylcarbazole and 2,4,7-trinitrofluoren-9-one as described in U.S. Pat. No. 3,484,237, an electrophotographic photoreceptor comprising poly-N-vinylcarbazole sensitized with a pyrylium salt-based dye as described in Japanese Patent Publication No. 25658/73, an electrophotographic photoreceptor with an organic pigment base as described in Japanese Patent Application (OPI) No. 37543/72 (the term "OPI" as used herein refers to a "published unexamined Japanese patent application"), and an electrophotographic photoreceptor having an eutectic complex comprising a dye and a resin as the main component as described in Japanese Patent Application (OPI) No. 10785/72.

In addition, an electrophotographic photoreceptor having copper phthalocyanine dispersed in a resin has also been described, particularly in Japanese Patent Publication No. 1667/77.

These organic electrophotographic photoreceptors have mechanical characteristics and flexibility improved to some extent as compared with the above-mentioned inorganic electrophotographic photoreceptors, but they have, in general, low photosensitivity and are not so suitable for extended repeated use, so that they are not fully satisfactory electrophotographic photoreceptors.

The photoconduction process of electrophotographic photoreceptors comprises:
(1) a process for generating electric charges through exposure, and
(2) a process for transporting electric charges.

As an example of electrophotographic photoreceptors in which the processes (1) and (2) are carried out by the same substance, there may be mentioned a selenium photosensitive plate. On the other hand, as an example of electrophotographic photoreceptors in which the processes (1) and (2) are each carried out by a different substance, a combination of amorphous selenium and poly-N-vinylcarbazole is well known. A function-separation type electrophotographic photoreceptor in which the processes (1) and (2) are each carried out by a different substance has advantages in that the range for selection of material can be extended, and consequently electrophotographic characteristics such as sensitivity and reception potential of the electrophotographic photoreceptor are improved, and substances suitable for preparation of coating film of electrophotographic photoreceptor can be selected from an extensive range.

Many function-separation type electrophotographic photoreceptors like this have been proposed, but only a few of these have been put into practice, and even those that have been put into practice have some deficiencies.

It has been proposed to select an electric charge transporting substance to be combined with an electric charge generating substance by taking the ionization potential as a standard, but such is a result of studies on electrophotographic photoreceptors prepared by selection of combination of specific materials of the same kind, so that it lacks generality and it cannot clearly account for electrophotographic characteristics of an electrophotographic photoreceptor prepared by selection between materials of different kinds.

The fact is that the combination of an electric charge generating substance with an electric charge transporting substance is studied largely by the method of trial and error at the present time. For example, with respect to electrophotographic photoreceptors that are characterized by an electric charge transporting substance, there have been made proposals described in Japanese Patent Application (OPI) Nos. 148749/82 (corresponding to U.S. Pat. No. 4,423,130), 19148/85, 95545/85, 186847/85 (corresponding to U.S. Pat. No. 4,594,304), 196767/85 (corresponding to U.S. application Ser. No. 06/713,720), and 35365/87 (corresponding to U.S. application Ser. No. 06/894,534). However, these proposed electrophotographic photoreceptors are still unsatisfactory in terms of sensitivity in a long wavelength region and, hence, realization of a photoreceptor having a higher sensitivity has been demanded.

SUMMARY OF THE INVENTION

An object of the invention includes providing an electrophotographic photoreceptor having high sensitivity and excellent durability.

In the invention, an electric charge generating layer is formed using a phthalocyanine pigment as an electric charge generating substance, which is selected from ε-type copper phthalocyanine, aluminum chloride phthalocyanine vanadyl phthalocyanine, X-type or τ-type phthalocyanine, indium chloride phthalocyanine, titanyl phthalocyanine, germanium chloride phthalocyanine, calcium chloride phthalocyanine, and magnesium phthalocyanine, one of the benzene rings of the aluminum chloride or indium chloride phthalocyanine being optionally monochlorinated, an electric charge transporting layer is formed using a hydrazone compound represented by formula (I) or (II) as set forth below as an electric charge transporting substance, and a lamination-type electrophotographic photoreceptor is formed through the combination of the above-mentioned layers. Thus, an electrophotographic photoreceptor having high sensitivity and excellent durability is obtained by the combination of both substances.

Thus the present invention is directed to an electrophotographic photoreceptor having a photosensitive layer disposed on a conductive substrate, the photosensitive layer having a laminated structure comprising an electric charge generating layer and an electric charge transporting layer, said electric charge generating layer containing a phthalocyanine pigment and said electric charge transporting layer containing at least one hydrazone compound represented by formula (I) or (II):

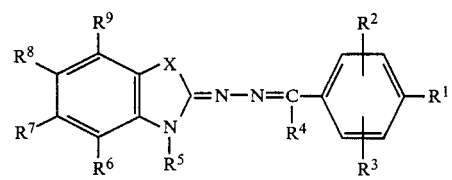
(I)

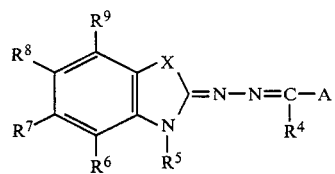
(II)

In formulae (I) and (II), X represents an oxygen atom, a sulfur atom, a selenium atom, a substituted or unsubstituted imino group, or a substituted or unsubstituted methylene group;

$R^1$ represents an alkoxy group, an aralkyloxy group, or a substituted amino group represented by

wherein $R^{10}$ and $R^{11}$ (which may be the same or different from each other) each represents a substituted or unsubstituted alkyl group, or a substituted or unsubstituted phenyl group, or $R^{10}$ and $R^{11}$ represent groups combined with each other to form an N-containing heterocyclic ring;

$R^2$ and $R^3$ (which may be the same or different from each other) each represents a hydrogen atom, a halogen atom, an alkyl group, or a lower alkoxy group;

$R^4$ represents a hydrogen atom, a substituted or unsubstituted alkyl group, or a substituted or unsubstituted phenyl group;

$R^5$ represents a substituted or unsubstituted alkyl group;

$R^6$, $R^7$, $R^8$, and $R^9$ (which may be the same or different from each other) each represents a substituted or unsubstituted alkyl, phenyl, alkoxy, or aralkyloxy group, a hydrogen atom, a halogen atom, or an amino group represented by

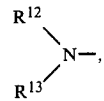

wherein $R^{12}$ and $R^{13}$ each represents a hydrogen atom or a group as defined for $R^{10}$ and $R^{11}$; or $R^6$, $R^7$, $R^8$, and $R^9$ combined with each other form a condensed carbocyclic ring or a condensed heterocyclic ring; and A represents a monocyclic heterocyclic 5-membered ring or a condensed heterocyclic 5-membered or 6-membered ring represented by one of formulae

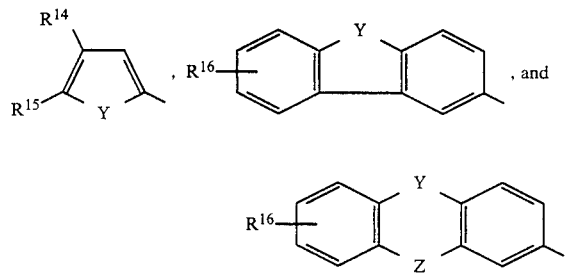

wherein Y and Z (which may be atoms of the same or different kind) each represents S, O, or N-$R^{17}$, wherein $R^{17}$ represents an alkyl group containing from 1 to 4 carbon atoms; and $R^{14}$ and $R^{15}$ (which are groups of the same or different kind) each represents a hydrogen atom, an alkyl group, or an alkoxy group, or $R^{14}$ and $R^{15}$ combine to form a benzene or naphthalene ring.

DETAILED DESCRIPTION OF THE INVENTION

The electrophotographic photoreceptor of the invention is prepared by forming a film layer containing a phthalocyanine pigment as an electric charge generating layer on a conductive substrate, and then laminating a layer containing a hydrazone compound represented by formula (I) or (II) as an electric charge transporting layer on the above-mentioned film layer.

As phthalocyanine pigments for the electric charge generating layer, ε-type phthalocyanine, aluminum chloride phthalocyanine, and vanadyl phthalocyanine are preferred, with ε-type phthalocyanine and aluminum chloride phthalocyanine being particularly preferred.

Aluminum chloride phthalocyanine used in the invention is represented by the formula

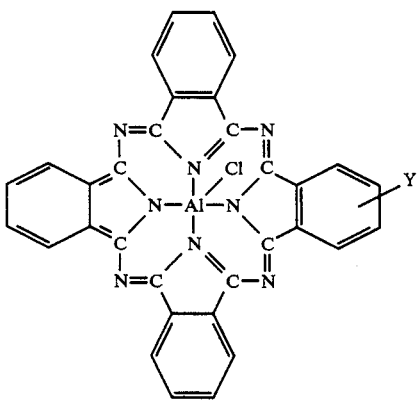

wherein Y represents a hydrogen or chlorine atom and one of benzene rings of the aluminum chloride phthalocyanine may be monochlorinated.

Aluminum chloride phthalocyanine can be synthesized readily by a known method. It can be synthesized by condensation of phthalic anhydride, aluminum chloride, and urea, in the presence or absence of a catalyst, or can be synthesized by use of phthalodinitrile instead of phthalic anhydride. Aluminum chloride phthalocyanine having one monochlorinated benzene ring can be synthesized readily by a method as mentioned in Japanese Patent Application (OPI) No. 211149/82.

Hydrazone compounds represented by the above-mentioned formula (I) or (II) which are used in an electric charge transporting layer in the invention are described in further detail below.

Specific examples of X in formulae (I) and (II) include oxygen, sulfur, and selenium atoms, alkylimino groups, a dimethylmethylene group, and the like. The alkyl group of the alkylimino group is an alkyl group containing from 1 to 8 carbon atoms. It is, in particular, preferred that X is a sulfur atom.

The alkoxy group and aralkyloxy group of $R^1$ include alkoxy groups containing from 1 to 12 carbon atoms and aralkyloxy groups containing from 1 to 12 carbon atoms, respectively, and specific examples of such groups include methoxy, ethoxy, propoxy, butoxy, octyloxy, and benzyloxy groups.

If $R^1$ represents a substituted amino group represented by

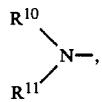

examples of the groups $R^{10}$ and $R^{11}$ include unsubstituted alkyl groups containing from 1 to 12 carbon atoms, such as methyl, ethyl, propyl, butyl, and the like, and substituted alkyl groups containing from 1 to 12 carbon atoms as set forth below.

The substituent group of substituted alkyl groups represented by $R^{10}$ and $R^{11}$ include alkoxy groups containing from 1 to 4 carbon atoms, aryloxy groups containing from 6 to 12 carbon atoms, a hydroxyl group, aryl groups containing from 6 to 12 carbon atoms, a cyano group, and halogen atoms. Preferred specific examples of substituted alkyl groups represented by $R^{10}$ and $R^{11}$ include (a) alkoxyalkyl groups such as methoxymethyl, methoxyethyl, ethoxymethyl, ethoxyethyl, ethoxypropyl, methoxybutyl, and propoxymethyl groups, (b) aryloxyalkyl groups such as phenoxymethyl, phenoxyethyl, naphthoxymethyl, and phenoxypentyl groups, (c) hydroxyalkyl groups such as hydroxymethyl, hydroxyethyl, hydroxypropyl, and hydroxyoctyl groups, (d) aralkyl groups such as benzyl, phenethyl, and ω,ω-diphenylalkyl groups, (e) cyanoalkyl groups such as cyanomethyl, cyanoethyl, cyanopropyl, and cyanobutyl groups, and (f) halogenated alkyl groups such as chloromethyl, bromomethyl, chloroethyl, bromopentyl, and chlorooctyl groups.

The phenyl group represented by the groups $R^{10}$ and $R^{11}$ may have a substituent group, and specific examples of such substituent groups include (a) alkyl groups containing from 1 to 12 carbon atoms, (b) alkoxy groups containing from 1 to 4 carbon atoms, (c) aryloxy groups containing from 6 to 7 carbon atoms, (d) acyl groups containing from 2 to 8 carbon atoms, (e) alkoxycarbonyl groups containing from 2 to 5 carbon atoms, (f) halogen atoms, (g) monoalkylamino groups having one substituent group comprising an alkyl group containing from 1 to 4 carbon atoms, (h) dialkylamino groups having two substituent groups each comprising an alkyl group containing from 1 to 4 carbon atoms, (i) amido groups containing 2 to 4 carbon atoms, and (j) a nitro group.

Examples of: (a) alkyl groups containing from 1 to 12 carbon atoms include methyl, ethyl, linear or branched propyl, butyl, pentyl, and hexyl groups; (b) alkoxy groups containing from 1 to 4 carbon atoms include methoxy, ethoxy, propoxy, and butoxy groups; (c) aryloxy groups include a phenoxy group and an o-, m-, or p-tolyloxy group; (d) acyl groups include acetyl, propionyl, benzoyl, and o-, m-, or p-toluoyl groups; (e) alkoxycarbonyl groups containing from 2 to 5 carbon atoms include methoxycarbonyl, ethoxycarbonyl, propoxycarbonyl, and butoxycarbonyl groups; (f) halogen atoms include chlorine, bromine, and fluorine atoms; (g) monoalkylamino groups having one substituent group comprising an alkyl group containing from 1 to 4 carbon atoms include methylamino, ethylamino, and butylamino groups; (h) dialkylamino groups having two substituent groups each comprising an alkyl group containing from 1 to 4 carbon atoms include dimethylamino, diethylamino, dipropylamino, dibutylamino, and N-methyl-N-ethylamino groups; and (i) amido groups include an acetamido group and propionamido group. As a heterocyclic ring formed by combination of $R^{10}$ and $R^{11}$, heterocyclic rings represented by the following formulae are preferred.

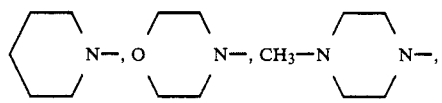

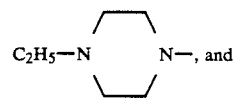

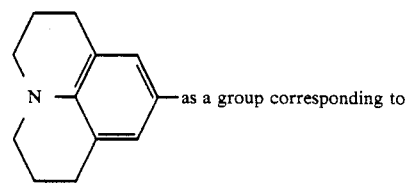

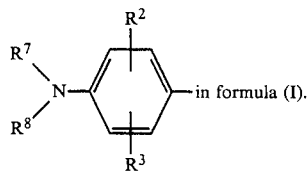

It is preferred that $R^1$ is a substituted amino group in which $R^{10}$ and $R^{11}$ each represents a methyl, ethyl, benzyl, phenyl, or tolyl group. In particular, substituted amino groups such as dimethylamino group, diethylamino group, dibenzylamino group, diphenylamino group, and N-ethyl N-phenylamino group are preferred.

Examples of $R^2$ and $R^3$ include the following: hydrogen atom; halogen atoms such as chlorine, bromine, and fluorine; alkyl groups containing from 1 to 4 carbon atoms such as methyl, ethyl, propyl, and butyl groups; and alkoxy groups containing from 1 to 4 carbon atoms such as methoxy, ethoxy, propoxy, and butoxy groups. Of these, a hydrogen atom, a methyl group, and a methoxy group are preferred.

Specific examples of $R^4$ include the following: hydrogen atom; alkyl groups containing from 1 to 4 carbon atoms such as methyl, ethyl, propyl, and butyl groups; and a substituted or unsubstituted phenyl group. The substituted phenyl group is the same as a substituted phenyl group represented by the above-mentioned $R^{10}$ or $R^{11}$. Preferred examples of $R^4$ are a hydrogen atom, a methyl group, an ethyl group, a phenyl group, and a p-(dimethylamino)phenyl group.

The substituted or unsubstituted alkyl group represented by $R^5$ is selected from the same members as the substituted or unsubstituted alkyl group represented by $R^{10}$ or $R^{11}$.

Examples of groups represented by each of $R^6$, $R^7$, $R^8$, and $R^9$ include substituted or unsubstituted alkyl and phenyl groups which are selected from the same members as the substituted or unsubstituted alkyl and phenyl groups represented by $R^{10}$ or $R^{11}$; a hydrogen atom; halogen atoms such as chlorine, bromine, and fluorine atoms; alkoxy groups containing from 1 to 12 carbon atoms such as methoxy group, ethoxy group, propoxy group, butoxy group, octyloxy group, and the like; aralkyloxy groups containing from 1 to 12 carbon atoms such as benzyloxy group, phenethyloxy group, and the like; and amino groups represented by

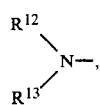

wherein $R^{12}$ and $R^{13}$ each represents a hydrogen atom or a substituted or unsubstituted alkyl or phenyl group represented by the above-mentioned $R^{10}$ or $R^{11}$. Further, $R^6$, $R^7$, $R^8$, and $R^9$ may combine with each other to form a condensed carbon ring such as naphthalene or a condensed heterocyclic ring. It is, in particular, preferred that they are hydrogen atoms. Groups $R^{14}$ and $R^{15}$ in the heterocyclic 5-membered ring

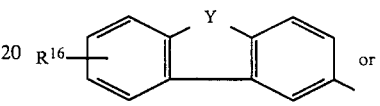

represented by A include: a hydrogen atom; alkyl groups containing from 1 to 4 carbon atoms such as methyl, ethyl, propyl, and butyl groups; alkoxy groups containing from 1 to 4 carbon atoms such as methoxy, ethoxy, propoxy, and butoxy groups; and groups able to combine with each other to form a benzene or naphthalene ring.

Examples of groups represented by $R^{16}$ in the condensed heterocyclic ring

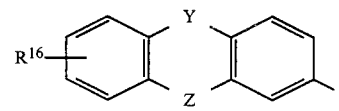

represented by A include: a hydrogen atom; a substituted or unsubstituted alkyl group which is the same as a substituted or unsubstituted alkyl group represented by the above-mentioned $R^{10}$ or $R^{11}$; an alkoxy group containing from 1 to 4 carbon atoms; an aryloxy group containing from 6 to 10 carbon atoms; an acyl group containing from 2 to 11 carbon atoms; an alkoxycarbonyl group containing from 2 to 5 carbon atoms; an aryloxycarbonyl group containing from 7 to 11 carbon atoms; a monoalkylamino group containing from 1 to 4 carbon atoms; a dialkylamino group containing from 1 to 4 carbon atoms; an amido group containing from 2 to 9 carbon atoms; and a nitro group. Further, these groups may have a substituent group.

The alkoxy group containing from 1 to 4 carbon atoms includes methoxy, ethoxy, propoxy, and butoxy groups; the aryloxy group includes phenoxy and o-, m-, or p-tolyloxy groups; the acyl group includes acetyl group, propionyl group, benzoyl group, and o-, m-, or p-toluoyl group; the alkoxycarbonyl group containing from 2 to 5 carbon atoms includes methoxycarbonyl group, ethoxycarbonyl group, propoxycarbonyl group, and butoxycarbonyl group; the aryloxycarbonyl group containing 7 to 11 carbon atoms includes phenoxycarbonyl group, and o-, m-, or p-tolyloxycarbonyl group; the halogen atoms include chlorine, bromine, and fluorine atoms; the monoalkylamino group having one substituent group comprising an alkyl group containing from 1 to 4 carbon atoms includes methylamino, ethylamino, and butylamino groups; the dialkylamino group having two substituent groups, each comprising an alkyl group containing from 1 to 4 carbon atoms includes dimethylamino, diethylamino, dipropylamino, dibutylamino, and N-methyl-N-ethylamino groups; the amido group includes acetamido and propionamido groups; and further, there is a nitro group as another substituent group.

As the heterocyclic ring represented by A, there may be mentioned 2-furyl group, 2-thienyl group, 1-methyl-2-pyrrolyl group, and 5-methyl 2-thienyl group as the heterocyclic 5-membered ring; 2-benzo[b]thienyl group, 2-naphtho[2,3-b]thienyl group, 9-ethylcarbazol-2-yl group, and dibenzothiophen-2-yl group as the condensed heterocyclic 5-membered ring; and 2-phenoxathienyl group, 10-ethylphenoxazin-3-yl group, and 10-ethylphenothiazin-3-yl group as the condensed heterocyclic 6-membered ring. Of these groups, a 5-methyl-2-thienyl group, 2-benzo[b]thienyl group, 9-ethylcarbazol-2-yl group, dibenzothiophen-2-yl group, and 10-ethylphenothiazin-3-yl group are preferred.

Specific examples of the hydrazone compound represented by formula (I) or (II) are shown below.

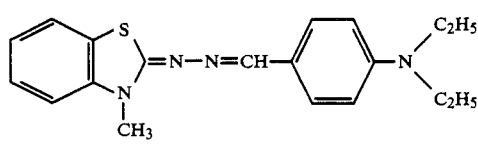
(1)

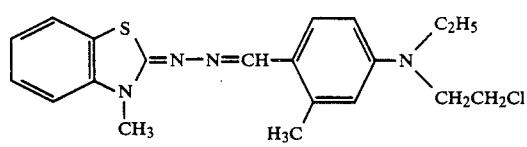
(2)

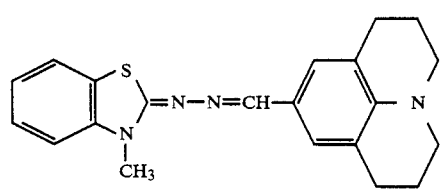
(3)

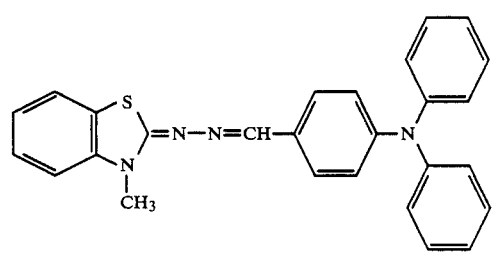
(4)

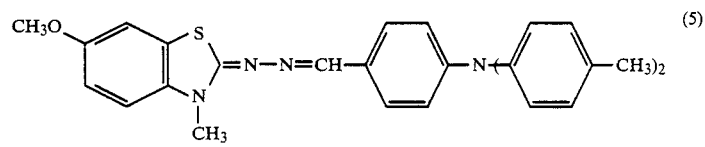
(5)

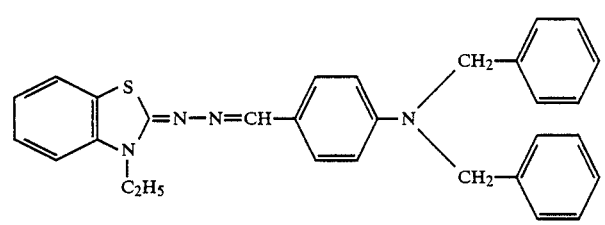
(6)

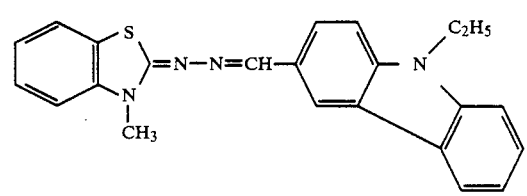
(7)

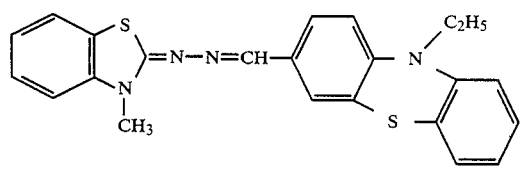
(8)
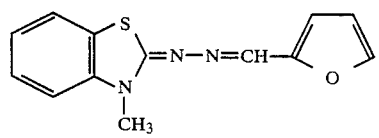
(9)
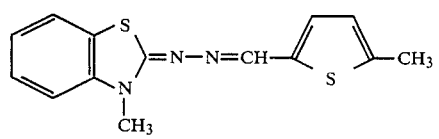
(10)
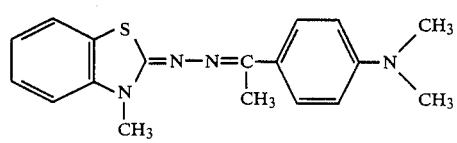
(11)
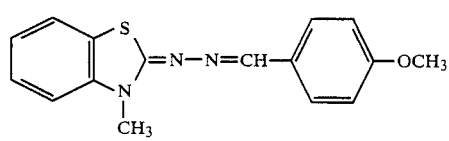
(12)
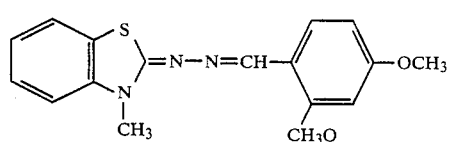
(13)
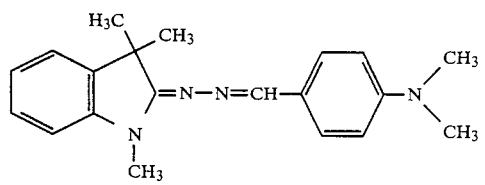
(14)
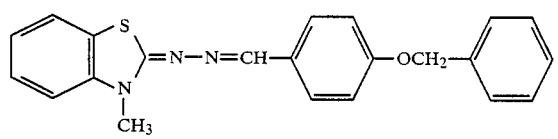
(15)
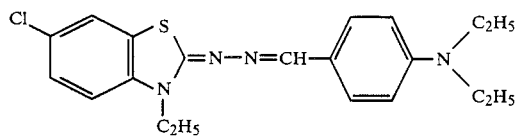
(16)
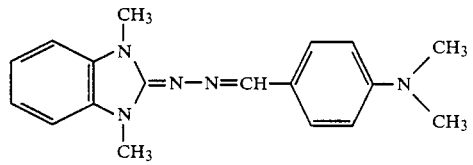
(17)
Hydrazone compounds represented by formula (I) or (II) can be readily prepared by a known method. The hydrazone compound can be prepared by a dehydration and condensation reaction of a heterocyclic hydrazine compound with a corresponding aldehyde or ketone in a solvent with the addition of a small amount of an acid (acetic acid or an inorganic acid) as a condensing agent, as required. As the solvent, alcohols such as methanol and ethanol, aromatic hydrocarbons such as benzene and xylene, dioxane, tetrahydrofuran, N,N-dimethylformamide, and the like can be used, in the form of a single compound or as a mixture of two or more compounds.

In laminating an electric charge transporting layer on an electric charge generating layer provided on a conductive substrate to form the electrophotographic photoreceptor of the invention, the electric charge generating layer can be formed by vacuum depositing phthalocyanine pigments on a conductive substrate or by dispersing fine powders of phthalocyanine pigments in an appropriate solvent or in a solvent having a binder dissolved in it, and then applying and drying the dispersion on the conductive substrate. The thickness of the electric charge generating layer is generally 5 microns or less, preferably 2 microns or less.

If the electric charge generating layer is formed by using and applying a binder, it is preferred that the amount of the phthalocyanine pigment used therein is at least 0.1 time the weight of the binder. If the phthalocyanine pigment is used in an amount less than 0.1 time the weight of the binder, sufficient sensitivity of the photoreceptor cannot be obtained.

The phthalocyanine pigment for use in an electric charge generating layer is pulverized into a fine powder having a particle size of 5 microns or less, preferably 2 microns or less, with a grinder such as ball mill, sand mill, vibratory mill, or the like.

On the thus formed electric charge generating layer, an electric charge transporting layer is disposed which contains a hydrazone compound represented by formula (I) or (II).

An electric charge transporting layer is disposed by dissolving a hydrazone compound represented by formula (I) or (II) in a solution of an appropriate binder and then applying and drying the resulting solution by a conventional method. The thickness of the electric charge transporting layer is generally from 3 to 20 microns, and preferably from 5 to 20 microns. The amount of the electric charge transporting substance used in an electric charge transporting layer is generally from 0.2 to 2 times the weight of the binder, and preferably from 0.3 to 1.3 times the weight of the binder.

In preparing the electrophotographic photoreceptor of the invention, an additive such as a plasticizer, a sensitizer, or the like may be used together with a binder.

As a conductive substrate used in the electrophotographic photoreceptor of the invention, a metallic sheet such as aluminum, copper, zinc, or the like, a plastic sheet or film such as polyester or the like having a conductive material such as aluminum, $SnO_2$, or the like vapor deposited or dispersed and applied on it, or paper electric conduction-treated is used.

As the binder, a high molecular polymer having hydrophobic properties, a high permittivity, and good forming properties for an electrically insulating film is preferably used. The high molecular polymers, for example, include the following polymers, but the binder is not limited thereto.

Polycarbonates, polyesters, methacylic resins, acrylic resins, polyvinyl chloride, polyvinylidene chloride, polystyrene, polyvinyl acetate, styrenebutadiene copolymers, vinylidene chloride-acrylonitrile copolymers, vinyl chloride-vinyl acetate copolymers, vinyl chloride-vinyl acetate-maleic anhydride copolymers, silicone resins, silicone alkyd resins, phenol-formaldehyde resins, styrene-alkyd resins, and poly-N-vinylcarbazole.

These binders can be used in the form of a single resin or of a mixture of two or more resins.

Examples of the plasticizer include biphenyl, biphenyl chloride, o-terphenyl, p-terphenyl, dibutyl phthalate, dimethyl glycol phthalate, dioctyl phthalate, triphenyl phosphate, methylnaphthalene, benzophenone, chlorinated paraffin, polypropylene, polystyrene, dilauryl thiodipropionate, 3,5-dinitrosalicylic acid, various fluorohydrocarbons, and the like.

In addition, a silicone oil or the like may be added to improve the surface properties of the electrophotographic photoreceptor.

Examples of sensitizers include chloranil and tetracyanoethylene.

An adhesion layer or a barrier layer may be disposed between the conductive substrate and the photosensitive layer. As materials used for these layers, there may be mentioned, besides the high molecular polymers used for the above-mentioned binder, gelatin, casein, polyvinyl alcohol, ethyl cellulose, carboxymethyl cellulose, a vinylidene chloride-based polymer latex as described in Japanese Patent Application (OPI) No. 84247/84, a styrene-butadiene-based polymer latex as described in Japanese Patent Application (OPI) No. 114544/84, aluminum oxide, and the like, and the thickness of the layer is preferably 1 micron or less.

The electrophotographic photoreceptor of the invention has been described in detail in the above, and it has characteristics of high sensitivity and excellent durability.

The electrophotographic photoreceptor of the invention can be used for electrophotographic copying machines, and, in addition, can be applied widely to fields such as photoreceptors of printers using a laser or cathode ray tube as a light source.

A photoconductive composition containing a hydrazone compound represented by formula (I) or (II) of the invention can be used as a photoconductive layer of an image pickup tube of video camera and also as a photoconductive layer of solid pickup element having a light receiving layer (photoconductive layer) disposed over known semi-conductor circuits arranged one dimensionally or two dimensionally for transfer of signals or for scanning.

Further, the photoconductive composition can also be used as a photoconductive layer of solar cell of the type described in A. K. Ghosh, Tom, Feng, *J. Appl. Phys.*, Vol. 49 (12), 5982 (1978).

The invention is described in further detail referring to examples hereinafter but it is not limited to these examples. "Parts" in the examples mean "parts by weight".

EXAMPLE 1

5 parts of ϵ-type copper phthalocyanine (Liophoton ® EPPC, a product of Toyo Ink MFG Co., Ltd.) and a solution prepared by dissolving 10 parts of polyester resin (Vylon ® 200, a product of Toyobo Co., Ltd.) in 100 parts of tetrahydrofuran were placed in a ball mill and they were ground and dispersed for 20 min. After that, the dispersion was applied to a conductive substrate (which was a polyethylene terephthalate film having a thickness of 75 microns, having an aluminum film vapor deposited on its surface that had a surface electric resistance of $10^3$ ohms) with a wire round rod and dried to prepare an electric charge generating layer having a thickness of 1 micron.

Next, a solution prepared by dissolving 3.6 parts of an electric charge transporting substance, that is, a compound No. 1, and 4 parts of a polycarbonate of bisphenol A in a mixture of 13.3 parts of dichloromethane and 26.6 parts of 1,2-dichloroethane was applied to the above-mentioned electric charge generating layer with a wire round rod and dried to form an electric charge transporting layer having a thickness of 11 microns. Thus, an electrophotographic photoreceptor having an electrophotographic sensitive layer comprising the abovementioned two layers was prepared.

The electrophotographic photoreceptor was electrified to $-600$ V by a corona discharge of -6 kV using a tesing apparatus for static electricity copying paper (SP-428 type, a product of Kawaguchi Denki Co.) and was then irradiated with light emitted from a tungsten lamp of color temperature of 3000° K. and providing illuminance of 2 lux on the surface of the photoreceptor. The time required for attenuation of surface potential from its original value to one-half of that value was measured to determine the exposure required for a reduciton by half, $E_{50}$ (lux.sec), and as a result, a value of 2.8 (lux.sec) of $E_{50}$ was obtained. The test comprising two processes of electrification and exposure was repeated 3000 times, and after that, the value of $E_{50}$ hardly changed.

COMPARATIVE EXAMPLES 1 TO 4

Various electrophotographic photoreceptors were prepared by the same method as in Example 1, except that a comparative compound as set forth below was used as an electric charge transporting substance instead of the hydrazone compound No. 1 used in Example 1, and the exposure for reduction by one-half was measured for each of the photoreceptors. The results are shown in Table 1.

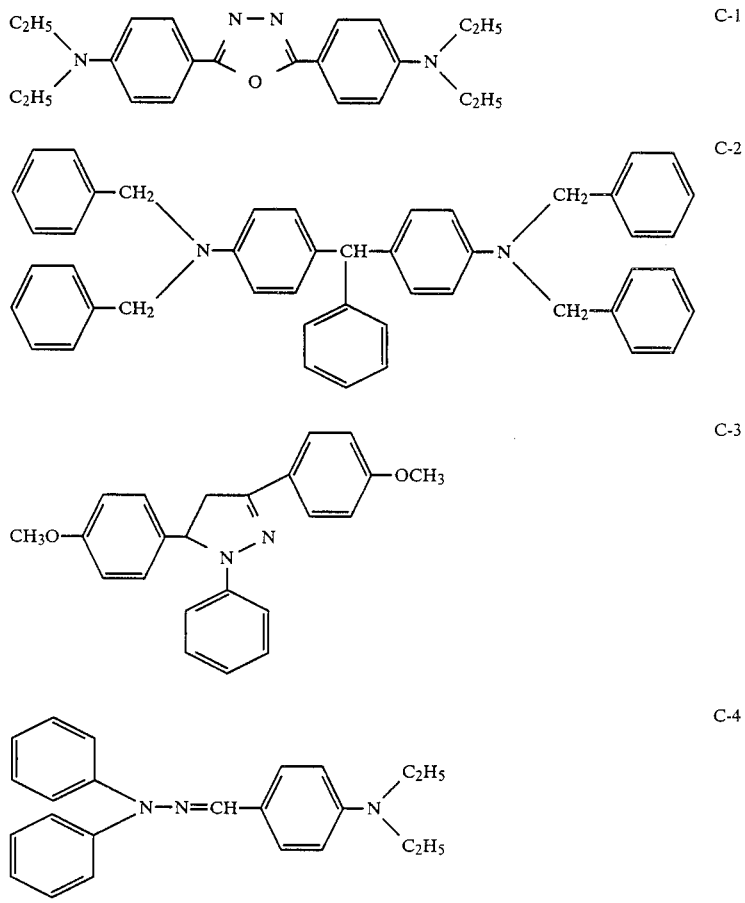

TABLE 1

| Comparative Example | Comparative Compound No. | $E_{50}$ [lux · sec] |
|---|---|---|
| 1 | C-1 | 19.3 |
| 2 | C-2 | 20.1 |
| 3 | C-3 | 18.5 |
| 4 | C-4 | 4.8 |

The test comprising two processes of electrification and exposure was repeated 3000 times for the electrophotographic photoreceptor of Example 1 and for Comparative Example 4. Measured values of $E_{50}$ are shown in Table 2.

TABLE 2

| | $E_{50}$ of 1st test | $E_{50}$ after testing 3000 times |
|---|---|---|
| Example 1 | 2.8 | 3.0 |
| Comparative Example 4 | 4.8 | 10.5 |

From the above results, it is clear that the photoreceptor of the invention has high sensitivity, and shows only a very small change in sensitivity after it is used repeatedly, and thus has excellent durability.

EXAMPLES 2 TO 8

Various electrophotographic photoreceptors were prepared by the same method as in Example 1, except that a hydrazone compound as shown in Table 3 was used as an electric charge transporting substance instead of hydrazone compound No. 1 used in Example 1.

TABLE 3

| Example | Electric charge transporting substance No. | $E_{50}$ (lux · sec) |
| --- | --- | --- |
| 2 | 3 | 2.5 |
| 3 | 4 | 2.1 |
| 4 | 7 | 3.2 |
| 5 | 8 | 3.6 |
| 6 | 10 | 4.4 |
| 7 | 13 | 5.0 |
| 8 | 17 | 2.7 |

From results of Table 3, it is seen that the electrophotographic photoreceptors of the invention have high sensitivity.

EXAMPLE 9

Aluminum chloride phthalocyanine was vapor deposited in a thickness of about 8000 Å on an aluminum substrate under a vacuum of $2 \times 10^{-6}$ Torr to form an electric charge generating layer.

A hydrazone compound No. 1 was used as the electric charge transporting substance, and an electrophotographic photoreceptor having a thickness of 12 microns was prepared by the same method as in Example 1.

The laminated photoreceptor was electrified to $-600$ V by a corona discharge of $-6$ kV. Monochromatic light produced by treating light from a light source of 500 W-Xe lamp with a monochromator (a product of Nippon Kogaku K.K.) was applied to the surface of the electrified photoreceptor and surface potential attenuation by light was measured.

An exposure for a reduction by half, $E_{50}$[erg/cm²], at 800 nm was 6.2 erg/cm²; thus, the photoreceptor had vary high sensitivity.

EXAMPLES 10 TO 15 AND COMPARATIVE EXAMPLE 5

Various electrophotographic photoreceptors were prepared by the same method as in Example 9, except that a compound as shown in Table 4 was used as an electric charge transporting substance instead of the hydrazone compound No. 1.

Measured results of an exposure for a reduction by half, $E_{50}$, for these photoreceptors are shown in Table 4.

TABLE 4

| Example | Electric charge transporting substance No. | $E_{50}$ (erg/cm²) |
| --- | --- | --- |
| 10 | 2 | 3.9 |
| 11 | 4 | 4.7 |
| 12 | 5 | 5.1 |
| 13 | 9 | 6.9 |
| 14 | 11 | 7.1 |
| 15 | 15 | 7.5 |
| Comparative Example 5 | Comparative Compound No. C-4 | 12.1 |

As is clearly shown by the results, the photoreceptor of the invention has high sensitivity and it has only a very small change of sensitivity after being used many times repeatedly, so that it has excellent durability. The effect has been obtained as a result of a combination of a phthalocyanine pigment with a hydrazone compound represented by the formula (I) or (II) in a lamination type electrophotographic photoreceptor.

While the invention has been described in detail and with reference to specific embodiments thereof, it will be apparent to one skilled in the art that various changes and modifications can be made therein without departing from the spirit and scope thereof.

What is claimed is:

1. An electrophotographic photoreceptor comprising a photosensitive layer disposed on a conductive substrate, said photosensitive layer having a laminated structure comprising an electric charge generating layer and an electric charge transporting layer, said electric charge generating layer containing a phthalocyanine pigment which is selected from ε-type copper phthalocyanine and aluminum chloride phthalocyanine, one of the benzene rings of the aluminum chloride phthalocyanine being optionally monochlorinated, and said electric charge transporting layer containing at least one hydrazone compound represented by formula (I) or (II)

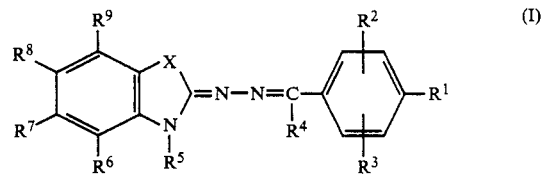

(I)

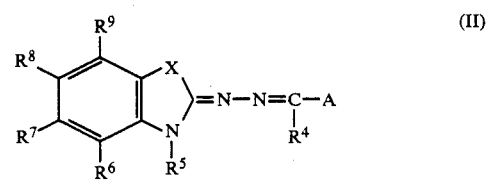

(II)

wherein

X represents an oxygen atom, a sulfur atom, a selenium atom, a substituted or unsubstituted imino group, or a substituted or unsubstituted methylene group;

$R^1$ represents an alkoxy group, an aralkyloxy group, or a substituted amino group represented by

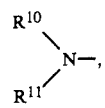

wherein $R^{10}$ and $R^{11}$ each represents a substituted or unsubstituted alkyl group, or a substituted or unsubstituted phenyl group, or $R^{10}$ and $R^{11}$ combine with each other to form an N-containing heterocyclic ring;

$R^2$ and $R^3$ each represents a hydrogen atom, a halogen atom, an alkyl group, or a lower alkoxy group;

$R^4$ represents a hydrogen atom, a substituted or unsubstituted alkyl group, or a substituted or unsubstituted phenyl group;

$R^5$ represents a substituted or unsubstituted alkyl group;

$R^6$, $R^7$, $R^8$, and $R^9$ each represents a substituted or unsubstituted alkyl, phenyl, alkoxy, or aralkyloxy group, a hydrogen atom, a halogen atom, or an amino group represented by

wherein $R^{12}$ and $R^{13}$ each represents a hydrogen atom or a group as defined for $R^{10}$ and $R^{11}$; or $R^6$, $R^7$, $R^8$, and $R^9$ combine with each other to form a condensed carbocyclic heterocyclic ring; and A represents a monocyclic heterocyclic 5-membered ring or a condensed heterocyclic 5-membered or 6-membered ring represented by one of formulae

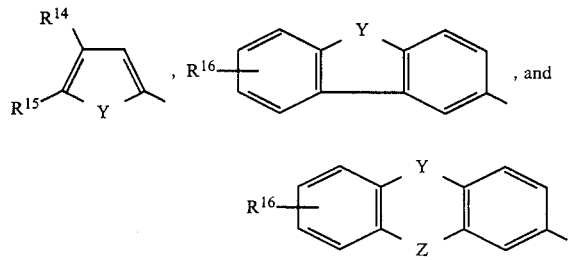

wherein Y and Z each represents S, O, or N-$R^{17}$, wherein $R^{17}$ represents an alkyl group containing from 1 to 4 carbon atoms; and $R^{14}$ and $R^{15}$ each represents a hydrogen atom, an alkyl group, or an alkoxy group, or $R^{14}$ and $R^{15}$ represent groups combined with each other to form a benzene or naphthalene ring.

2. An electrophotographic photoreceptor as in claim 1, wherein $R^1$ is a substituted amino group, represented by

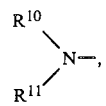

wherein $R^{10}$ and $R^{11}$ each represents a methyl, ethyl, benzyl, phenyl or tolyl group;

$R^2$ and $R^3$ each represents a hydrogen atom, a methyl group, or a methoxy group;

$R^4$ represents a hydrogen atom, a methyl group, an ethyl group, a phenyl group, or a p-(dimethylamino)phenyl group;

$R^5$ represents a methyl or ethyl group;

$R^6$, $R^7$, $R^8$, and $R^9$ each represents a hydrogen atom; and

A represents a 5-methyl-2-thienyl group, a 2-benzo[b]thienyl group, a 9-ethylcarbazol-2-yl group, a dibenzothiophen-2-yl group, or a 10-ethylphenothiazin-3-yl group.

3. An electrophotographic photoreceptor as in claim 1, wherein said electric charge generating layer has a thickness of 2 microns or less.

4. An electrophotographic photoreceptor as in claim 2, wherein said electric charge generating layer has a thickness of 2 microns or less.

5. An electrophotographic photoreceptor as in claim 1, wherein said electric charge transporting layer has a thickness of from 5 to 20 microns.

6. An electrophotographic photoreceptor as in claim 2, wherein said electric charge transporting layer has a thickness of from 5 to 20 microns.

7. An electrophotographic photoreceptor as in claim 1, wherein said electric charge transporting layer further comprises a binder, and the amount of the hydrazone compound in said electric charge transporting layer is from 0.3 to 1.3 times the weight of the binder.

* * * * *